(12) United States Patent  (10) Patent No.: US 8,278,628 B2
Hamilton  (45) Date of Patent: Oct. 2, 2012

(54) APPARATUS AND PROCESS FOR STERILIZATION AND PRESERVATION OF OBJECTS

(76) Inventor: Timothy Hamilton, Griffin, GA (US)

( * ) Notice: Subject to any disclaimer, the term of this patent is extended or adjusted under 35 U.S.C. 154(b) by 863 days.

(21) Appl. No.: 12/062,221

(22) Filed: Apr. 3, 2008

(65) Prior Publication Data

US 2009/0068071 A1  Mar. 12, 2009

Related U.S. Application Data

(60) Provisional application No. 60/909,811, filed on Apr. 3, 2007.

(51) Int. Cl.
 *G01N 23/00* (2006.01)
 *H01J 37/20* (2006.01)

(52) U.S. Cl. ............. 250/455.11; 250/453.11; 442/22; 442/23; 442/24; 442/28; 442/116; 442/118; 442/186.3; 442/186.07

(58) Field of Classification Search ........... 250/455.11, 250/453.11; 442/22–24, 28, 116, 118, 186.3, 442/186.07
See application file for complete search history.

(56) References Cited

U.S. PATENT DOCUMENTS

2002/0119072 A1* 8/2002 Bushnell et al. ............... 422/22
2006/0263276 A1* 11/2006 Pattee ...................... 422/186.07

FOREIGN PATENT DOCUMENTS

WO  WO2007/106888  * 9/2007
WO  WO2007/146699  * 12/2007

* cited by examiner

*Primary Examiner* — Jack Berman
*Assistant Examiner* — Meenakshi Sahu
(74) *Attorney, Agent, or Firm* — Donald R. Andersen, Esq.; Stephen J. Weyer, Esq.; Stites & Harbison, PLLC

(57) ABSTRACT

This apparatus and method improves the way metal and other objects will be sterilized, disinfected and preserved by utilizing both electromagnetic radiation (UV light in particular) to kill anaerobic pathogens and oxygen depletion to kill aerobic pathogens. The removal of the presence of oxygen further increases the useful lifespan of the treated object by preventing corrosion in general and oxidation in particular.

10 Claims, 2 Drawing Sheets

APPARATUS AND PROCESS FOR STERILIZATION AND PRESERVATION OF OBJECTS

CROSS REFERENCE TO RELATED APPLICATIONS

This application claims benefit of U.S. Provisional Application No. 60/909,811, filed Apr. 3, 2007 (which is hereby incorporated by reference).

BRIEF SUMMARY OF THE INVENTION

An improved apparatus and process for sterilization and preservation of objects is disclosed that can be used to disinfect, sterilize and preserve metal objects through the use of ultraviolet light. Although machines that sterilize metal objects through the use of ultraviolet light already exist, the preferred embodiment of the apparatus and process sterilizes metal using a new and novel apparatus and method, in which a vacuum is created that will remove all of the air and oxygen from the container containing the metal object that is to be sterilized with ultraviolet radiation. This process of removing air from the container and replacing the air with inert gas has two advantages: 1) decreases the pathogenicity of aerobic flora and therefore aerobic pathogens will die in the absence of $O_2$ and the object will remain sterilized and 2) the metal object will not oxidize or rust.

DETAILED DESCRIPTION OF THE INVENTION

Figure 1:
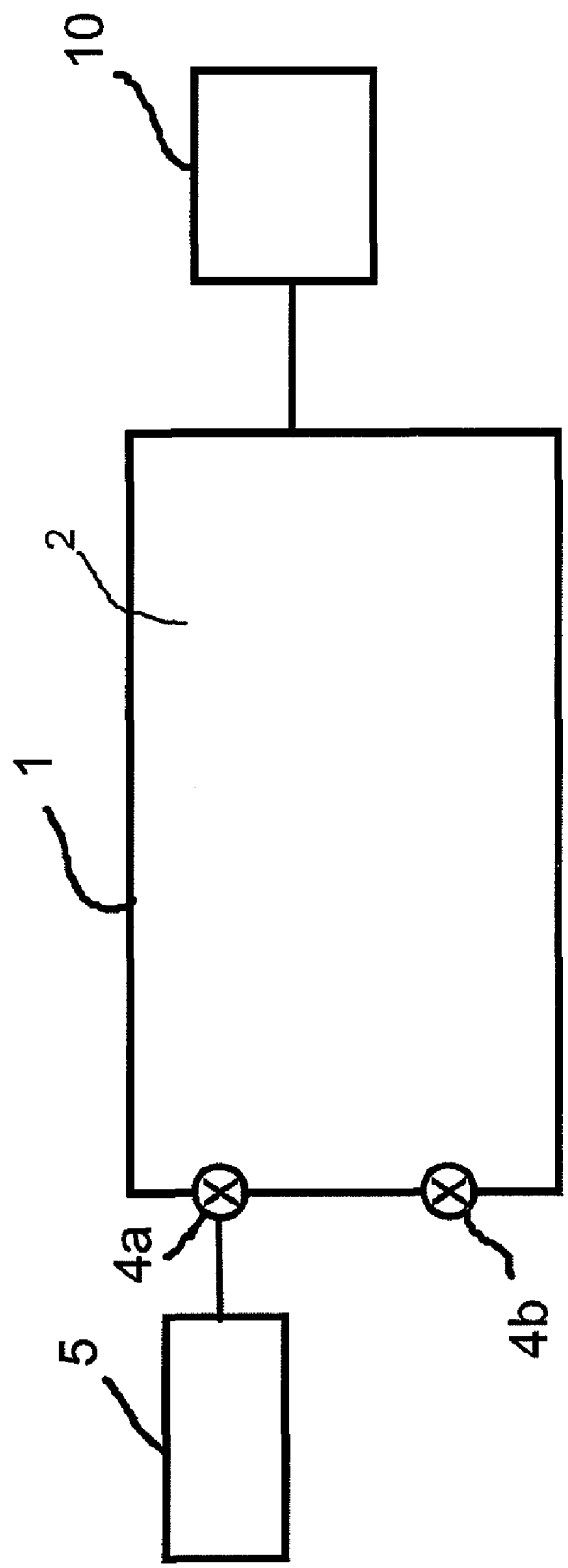
FIG. 1 is a schematic diagram showing a preferred embodiment of the present invention.
Figure 2:
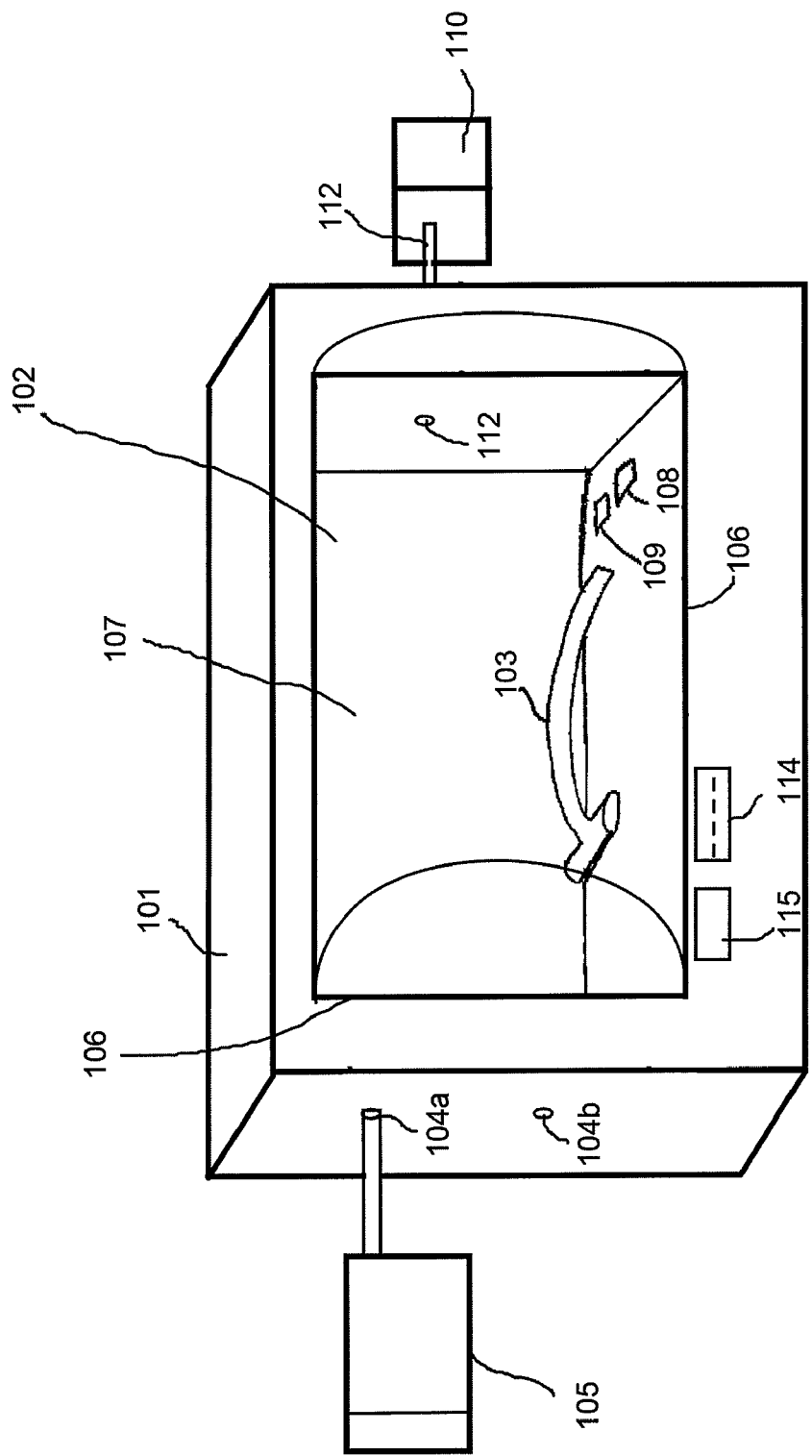
FIG. 2 is a drawing of a preferred embodiment of the present invention.

Referring now to the drawings where FIG. 1 is a schematic drawing of a general embodiment of the present invention and FIG. 2 is a further specific preferred embodiment, reference numbers in FIG. 2 which correspond to elements in FIG. 1 have been raised by 100. Only unique elements to FIG. 2 will be discussed separate from the elements in the general embodiment of FIG. 1.

The apparatus will include a canister 1, 101 having a work chamber 2, 102 into which the object 103 (FIG. 2) to be sterilized, disinfected and preserved is inserted and secured. The canister 1, 101 will be a (preferably) clear material (including but not limited to glass, composite plastic, or metal). The canister 1, 101 will be constructed in order to achieve and maintain an ideal vacuum. It will open sufficiently to allow emplacement of the target object. The canister 1, 101 could be lined with a reflective material. Two airtight valves 4a, 104a and 4b, 104b will be incorporated into the apparatus to allow the removal of air and the introduction of an inert gas (such as nitrogen) into the chamber 2, 102. The source at the inert gas would be a separate tank or a gas generator 5, 105. The exchange of gas for the vacuum will allow for reduction of pressure on the valve seals 4a, 104a and 4b, 104b (which will maintain structural integrity of the chamber 2, 102 and the seals 106 (FIG. 2)) and will allow for a continued decrease in aerobic pathogenesis. The source of the nitrogen gas can be a tank or a nitrogen generator 5, 105 that separates nitrogen gas from the air. The exchange of the gases will reduce the pressure on the airtight seals 106. Furthermore, it will ensure the cessation of oxidation and death of aerobic pathogens which need oxygen to survive.

The chamber 2, 102 will include compartment such as compartment 107 which will be exposed to the vacuum. Referring specifically to FIG. 2, chamber 2, 102 will contain a desiccant 108 such as silica gel to remove $H_2O$. The chamber 102 also will contain an oxygen scavenger 109 to remove $O_2$.

The intensity of the electromagnetic radiation source 110 varies inversely with the square of the distance from the source. The electromagnetic radiation source 10, 110 should in close proximity to the object to be sterilized, such as object 103 being exposed. The source of the electromagnetic radiation either inside of the canister 1, 101 or outside of the canister 1, 101. A cable 12, 112 could be used to transmit the wavelengths of interest to the inside of the canister.

UV light will degrade plastic, therefore, the canister 1, 101 should be made of a UV-resistant material that will not degrade as quickly.

Depending upon the scale of the target objects, the vacuum needed for atmospheric replacement may be done by a large electronic or smaller hand pump 5, 105. There are several options for the production of a vacuum. For larger scale industrial use or hospital use, a large vacuum pump can be used. For residential use, a hand pump could be utilized.

Again, referring to the embodiment of FIG. 2, a timer 114 will be incorporated with an on/off switch 115 to indicate the completion of the process and to control the electromagnetic radiation source. The user will have the option of keeping the sterilized and disinfected object in the canister 1, 101 in the non corrosive atmosphere until ready for use.

What is claimed is:

1. An apparatus for sterilization and preservation of metal objects using electromagnetic radiation, comprising:
    a housing provided with openings for insertion of said metal objects;
    a means for achieving a vacuum-tight seal of the openings in said housing and thereby allowing a vacuum to be created and maintained within the housing;
    a light source which generates electromagnetic radiation directed toward metal objects within said housing;
    at least two valves to allow for the removal and introduction of gaseous substances; and
    a means for removing air from inside the housing to thereby create a vacuum in the housing.

2. The apparatus of claim 1, wherein the means for removing air comprises means for removing oxygen.

3. The apparatus of claim 1, wherein the means for removing air generates a vacuum within the housing.

4. The apparatus of claim 1, wherein the light source generates UV light which is directed into the housing for sterilizing and preserving metal objects placed therein.

5. The apparatus of claim 4, wherein the light source generates an electromagnetic radiation sufficient to sterilize metal objects within the housing.

6. The apparatus of claim 1, further comprising a gas source for generating gas to be pumped into the housing.

7. The apparatus of claim 6, wherein the gas source generates an inert gas to be pumped into the housing.

8. The apparatus of claim 7, wherein the inert gas is nitrogen.

9. The apparatus of claim 1, wherein the housing is a canister.

10. The apparatus of claim 1, wherein the housing is lined with reflective material.

* * * * *